United States Patent
Greenhut et al.

(10) Patent No.: US 7,191,003 B2
(45) Date of Patent: Mar. 13, 2007

(54) STIMULATION ARRANGEMENT WITH STIMULATION SUCCESS MONITORING

(75) Inventors: Saul E. Greenhut, Aurora, CO (US); Tibor Nappholz, Evergreen, CO (US); Gary Schneider, Castle Rock, CO (US); Max Schaldach, deceased, late of Erlangen (DE); by Max Schaldach, Jr. legal representative, Berlin (DE)

(73) Assignee: Biotronik Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 663 days.

(21) Appl. No.: 10/047,999

(22) Filed: Jan. 15, 2002

(65) Prior Publication Data

US 2002/0138111 A1 Sep. 26, 2002

(30) Foreign Application Priority Data

Jun. 8, 2001 (DE) ................. 101 28 982

(51) Int. Cl.
*A61N 1/00* (2006.01)
(52) U.S. Cl. ........................................ 607/27
(58) Field of Classification Search .............. 607/9, 607/27
See application file for complete search history.

(56) References Cited

U.S. PATENT DOCUMENTS

| | | | |
|---|---|---|---|
| 4,773,401 A | 9/1988 | Citak et al. | |
| 5,107,834 A * | 4/1992 | Ideker et al. | 607/5 |
| 5,172,690 A | 12/1992 | Nappholz | |
| 5,417,718 A | 5/1995 | Kleks et al. | |
| 5,443,485 A | 8/1995 | Housworth et al. | |
| 5,571,144 A | 11/1996 | Schroeppel | |
| 5,697,957 A | 12/1997 | Noren et al. | |
| 5,800,467 A | 9/1998 | Park et al. | |
| 5,861,012 A | 1/1999 | Stroebel | |
| 5,861,013 A | 1/1999 | Peck et al. | |
| 5,873,898 A | 2/1999 | Hemming et al. | |
| 5,941,903 A | 8/1999 | Zhu et al. | |
| 5,954,756 A | 9/1999 | Hemming et al. | |
| 6,154,674 A | 11/2000 | Meier | |
| 6,175,766 B1 | 1/2001 | Bornzin | |
| 6,339,724 B1 | 1/2002 | Thong | |
| 6,571,129 B2 | 5/2003 | Schaldach | |
| 2004/0138718 A1 | 7/2004 | Limousin et al. | |

FOREIGN PATENT DOCUMENTS

DE 3447892 7/1986

(Continued)

OTHER PUBLICATIONS

European Examination Report.

*Primary Examiner*—Mark Bockelman
(74) *Attorney, Agent, or Firm*—Hahn Loeser & Parks, LLP; David J. Muzilla (57) ABSTRACT

A stimulation arrangement having a stimulation unit for the delivery of electrical pulses for the stimulation of body tissue and an evaluation unit which receives electrical signals in conjunction with the delivery of a stimulation pulse and evaluates same for checking a stimulation success, wherein the evaluation unit detects in the received signal such signal features which characterize a lack of stimulation success and delivers a corresponding signal.

19 Claims, 4 Drawing Sheets

FOREIGN PATENT DOCUMENTS

| | | |
|---|---|---|
| DE | 199 29 091 A1 | 12/2000 |
| DE | 199 29 553 A1 | 1/2001 |
| DE | 10007715 | 8/2001 |
| EP | 0447024 A2 | 1/1991 |
| EP | 0793976 A2 | 3/1997 |
| EP | 0 826 392 A2 | 3/1998 |
| EP | 0941744 | 9/1999 |
| EP | 1062974 A | 12/2000 |

* cited by examiner

STIMULATION ARRANGEMENT WITH STIMULATION SUCCESS MONITORING

CROSS-REFERENCE TO RELATED APPLICATIONS

[Not Applicable]

STATEMENT REGARDING FEDERALLY SPONSORED RESEARCH OR DEVELOPMENT

[Not Applicable]

INCORPORATION BY REFERENCE

[Not Applicable]

TECHNICAL FIELD OF THE INVENTION

The invention concerns a stimulation arrangement having a stimulation unit which is adapted to deliver electrical stimulation pulses for the stimulation of body tissue, and an evaluation unit which is adapted to receive electrical signals in conjunction with the delivery of a stimulation pulse and to evaluate same for checking stimulation success.

BACKGROUND OF THE ART

The invention concerns in particular a cardiac pacemaker as is usually employed to ensure by means of electrical pulses to the myocardium of a heart a cardiac rhythm which does justice to the hemodynamic demand of a patient. Such pacemakers are usually connected by way of an electrode line to electrodes which are suitable for intracardial arrangement and for electrical stimulation of the heart tissue (myocardium) by delivering electrical pulses to the myocardium. As such pacemakers are usually implanted, it is a matter of particular significance that the amount of energy delivered with an electrical stimulation pulse is precisely such that the heart tissue is safely and reliably stimulated. A stimulation pulse which is excessively rich in energy would excessively rapidly drain the battery of the pacemaker. On the other hand, a stimulation pulse which was too low in energy would possibly not suffice to excite the heart tissue in the sense of a stimulus which appropriately propagates and results in contraction of a corresponding chamber of the heart.

With that background in mind it is known, in conjunction with the delivery of a stimulation pulse to the myocardium, to implement a check in respect of the success of stimulation by the evaluation of electrical signals which occur in conjunction with the delivery of the stimulation pulse, in order for example in the case of an absence of stimulation success to be able to trigger a backup stimulation pulse with a higher energy content. Stimulation success monitoring presupposes the detection of successful stimulation which is also known as capture recognition. Numerous devices and methods are known which are intended to permit capture recognition.

A large number of systems for automatic capture detection have already been developed, which in connection with cardiac pacemakers serve to detect the presence/absence of depolarisation of the myocardium following a stimulation pulse. Those systems usually employ very simple methods such as evaluation of the signal amplitude—that is to say, the maximum amount of the signal—in order to detect myocardium depolarisation which characterises stimulation success, and in that way to distinguish same from signals which are involved with a lack of stimulation success. Such systems operate satisfactorily as long as the polarisation voltage is low and a typical signal which characterises stimulation success occurs. However, the result of the fusion of stimulated and natural cardiac reactions (a fusion event) can be that the signal following a stimulation pulse is atypical and is attributed by a simple algorithm to a lack of stimulation success. In addition, strong polarisation voltages can simulate a signal which is characteristic of successful stimulation. There is therefore a problem in reliably detecting the electrical signals evoked in the myocardium in the presence of such signal artefacts which are due for example to polarisation effects in the region of the interface between an electrode and body fluid or myocardium.

Various ways of resolving the last-mentioned problem are proposed for example in U.S. Pat. No. 5,417,718 to Kleks (23 May 1995), U.S. Pat. No. 5,697,957 to Noren (16 Dec. 1997), U.S. Pat. No. 5,861,013 to Peck (19 Jan. 1999), U.S. Pat. No. 5,873,898 to Hemming (23 Feb. 1999, and U.S. Pat. No. 5,941,903 to Zhu (24 Aug. 1999), as well as European patent application EP 0 826 392, also to Noren.

It is also known to detect characteristic evoked signals on the basis of typical signal shapes, for a positive stimulation success.

Unfortunately recognition of stimulation success is tainted in all cases with statistical uncertainties so that there is still a wish to implement capture recognition with a higher level of specificity and sensitivity.

SUMMARY OF THE INVENTION

In accordance with the invention, that is achieved with a stimulation arrangement of the kind set forth in the opening part of this specification, in that the evaluation unit is adapted to detect in the received signal such signal features which characterise a case of lack of stimulation success, and to deliver a corresponding output signal.

The essential difference in relation to the state of the art is therefore that a lack of stimulation success is not ascertained in a reversal procedure by virtue of non-detection of signal features characterising a stimulation success, but directly by the detection of signal features which characterise a lack of stimulation success. Stimulation success recognition in the state of the art is based on detecting signal features which characterise a positive stimulation success and inferring a lack of stimulation success from the non-appearance of such signal features which characterise a positive stimulation success.

In accordance with the present invention it is precisely the opposite way that is adopted, which is based on the realisation that there are actually signal features which are specific for a lack of stimulation success and which are not merely based on the absence of such signal features which characterise a positive stimulation success. The arrangement according to the invention therefore detects signal features, about the presence and the significance of which no indications are to be found in the state of the art.

The invention is based in particular on the realisation that a signal following a stimulation pulse has two separate signal elements, more specifically on the one hand a first signal element which is due to polarisation of the myocardium and on the other hand a second signal element which is based on polarisation in the region of the body fluid or tissue adjoining the stimulation electrode. That polarisation effect in the region of the electrode interface represents wasted energy and results in a signal which interferes with the positive detection of an evoked signal following a stimulation operation. Admittedly, modern electrode lines, for example fractal electrode lines, are designed in such a way that the polarisation potentials are reduced as much as possible. That is typically achieved by way of an increase in electrode area by means of micro-structuring, whereby capacitive effects are reduced. Although polarisation is reduced with such electrodes however, it is not entirely eliminated. In addition, the electrodes vary within and between various design series in terms of their effectiveness in the reduction of polarisation potentials. And even the best electrodes, with stimulation amplitudes of more than 2 volts, exhibit measurable signal artefacts to be attributed to polarisation, even still 20 milliseconds after a stimulation pulse. The amplitude of that artefact increases the voltage and broadens the stimulation pulse.

In the stimulation arrangement according to the invention, in a preferred embodiment thereof, it is provided for the first time that signal artefacts which are characteristic of polarisation are detected as a signal feature which characterises a lack of stimulation success.

This preferred embodiment is based on the realisation that signal artefacts of that kind which are to be attributed to polarisation regularly have a similar morphology. That realisation was obtained by tests in which electrode lines were investigated in a salt solution in respect of the signal shapes which occur subsequently to the delivery of a pulse to the salt solution.

On the other hand it was observed that electrograms recorded in a human being can assume virtually any form. Such variations in electrogram morphologies can occur both in the case of various measurements on a patient and also in the case of measurement on different patients. Differences between the measurements on a patient typically occur due to fusion events, respiration influences of anodal stimulation or other unidentified reasons. Differences between measurements on different patients presumably arise out of differences in cardiac pathology, the electrode line position or electrode polarisation.

On the basis of the polarisation signal shape, characteristic features, signatures of polarisation potential in the form of a plurality of signal features and threshold values were extracted. Preferred configurations of the invention are directed to those signal features and threshold values.

The features which are preferably detected include a first integral INGR1 of the signal measured after the expiry of a blanking period after the delivery of a stimulation pulse over time up to the moment in time at which the measured signal crosses the signal value which obtains during the blanking period. That first signal is generally positive as the signal measured subsequently to the blanking period is usually above the signal value during the blanking period. The evaluation unit is preferably correspondingly adapted to determine the first integral INGR1.

A further preferably received and ascertained signal feature is a second integral INGR2 of the measured signal which is formed over a period of time beginning with the moment in time at which the first integral ends and which ends with the end of a predetermined time window, the predetermined time window beginning with the expiry of the blanking period. Accordingly the evaluation unit is preferably adapted also to determine the second integral INGR2.

A further signal feature which is preferably recorded by a suitably designed evaluation unit is the number CNT1 of the sample values of the recorded signal, which fall into the period of time over which the first integral is formed. In that case the stimulation arrangement is adapted to sample the recorded signal in time-discrete manner so that the recorded signal is present in the form of a plurality of time-discrete sample values or samples. The evaluation unit preferably has a counter for counting the sample values within a period of time.

A further signal feature which is additionally or also alternatively received is an indicator flag CROSS whose value depends on whether the measured signal, during the period of time for determining the second integral, crosses the signal amplitude which obtains during the blanking period. If the signal value forms the reference or zero value during the blanking amplitude for the subsequently measured signal, the indicator flag CROSS=1 characterises the presence of a zero-passage for the measured signal during the time over which the second integral is formed. If no zero-passage exists the indicator flag is CROSS=0. The evaluation unit is preferably adapted to determine and store the binary value of the indicator flag CROSS.

A further signal feature is the maximum positive sample value of the measured signal received after the conclusion of the blanking period, with the first x sample values after expiry of the blanking period being disregarded. Therefore preferably the x+1st sample value after expiry of the blanking period is recorded as the maximum positive sample value MAX_POS. The sample value—like the entire signal measured after the expiry of the blanking period—is determined relative to the signal amplitude which obtains during the blanking period. In addition preferably all sample values which are negative in relation to the signal amplitude during the blanking period are stored as NEG_AMP. The evaluation unit is accordingly preferably adapted to determine the maximum positive sample value MAX_POS and the negative sample values NEG_AMP and to store those values.

For further analysis of the signal features determined in the above-described manner, the evaluation unit preferably has various threshold value units which essentially include a store or memory for the respectively predetermined value of the corresponding threshold value, and a comparison unit which delivers a signal which depends on whether the value exceeds or is below the predetermined threshold value. The following threshold values or parameters are preferably provided:

w width of the time window in milliseconds or number of sample values w1 limit value for a first positive signal portion which is given by the number of sample values, over which the first integral is formed (CNT1)

zn negative limit value for the sample values related to the signal amplitude during the blanking period zp limit value for the maximum positive sample value MAX_POS if the positive signal portion is wider than is predetermined by w1 a1 a limit value for an area AREA which is formed from the first and second integrals (INGR1, INGR2) as a characteristic of non-capture a2 a limit value for the area AREA, above which there is a capture x the above-mentioned number of sample values after the end of the blanking period, which are ignored for determining MAX_POS.

The evaluation unit is further preferably adapted to implement ascertainment of a non-successful stimulation procedure (non-capture), based on the previously introduced signal features and limit values, in accordance with the following algorithm:

If NEG_AMP<zn Then Capture

If CNT1>w1 Then AREA=INGR1+INGR2 Else AREA= INGR2

If AREA<a1 Then Non-Capture

Elseif CNT1>w1 Then (If MAX_POS<zp Then Non-Capture Else Capture)

Elseif AREA>a2 Then Capture

Elseif CROSS=1 Then Capture

Else Non-Capture

The evaluation unit is thus preferably adapted to implement the following threshold value comparisons and furnish corresponding results:

If NEG_AMP is greater than zn the evaluation unit outputs a capture signal characterising successful stimulation.

If the number of sample values CNT1 is greater than w1, then the area value AREA is formed as a sum from the first integral INGR1 and the second integral INGR2, otherwise the area value AREA is equal to the second integral INGR2. The area AREA is then compared to the threshold value a1 and if AREA is less than a1 a non-capture signal characterising unsuccessful stimulation is outputted. If that condition is not fulfilled the evaluation unit checks whether the number CNT1 is greater than the limit value w1 and, if that is the case, effects a comparison of the maximum positive sample value MAX_POS with the limit value zp. If MAX_POS is smaller than zp, a non-capture signal is outputted, otherwise it is a capture signal. If neither of the two conditions AREA is smaller than a1 and CNT1 is greater than w1 are given, the evaluation unit compares the area value AREA to the limit value a2 and, in the case where AREA is greater than a2, outputs a capture signal. If that condition also does not apply, the evaluation unit checks whether the indicator flag CROSS is set to 1, that is to say whether the measured signal has a zero-passage in the region of the second integral. In that case a capture signal is outputted. If that condition also does not apply the evaluation unit outputs a non-capture signal.

In addition the evaluation unit is preferably adapted to already implement continuously a comparison of the sample values with the threshold value for the negative signal amplitude upon receiving the sample values for the measured signal. If a negative sample value NEG_AMP is smaller than zn (or in other words, is of a greater negative amount than zn), the measured signal is immediately classified as a signal characterising stimulation success and accordingly a capture signal is outputted. That checking operation is preferably carried out by the evaluation unit sample value by sample value in parallel with the above-described algorithm, and interrupts that algorithm immediately if a sample value NEG_AMP is smaller than zn. The above-described algorithm is continued to the end only when the condition NEG_AMP<zn is not fulfilled while the sample values are being received. That advantageously saves on computing capacity and energy.

In this respect a brief description of the preferred configuration of the invention.

BRIEF DESCRIPTION OF THE DRAWINGS

It will now be described in greater detail by means of an embodiment given by way of example and with reference to the Figures in which.

DETAILED DESCRIPTION OF THE INVENTION

Figure 1:
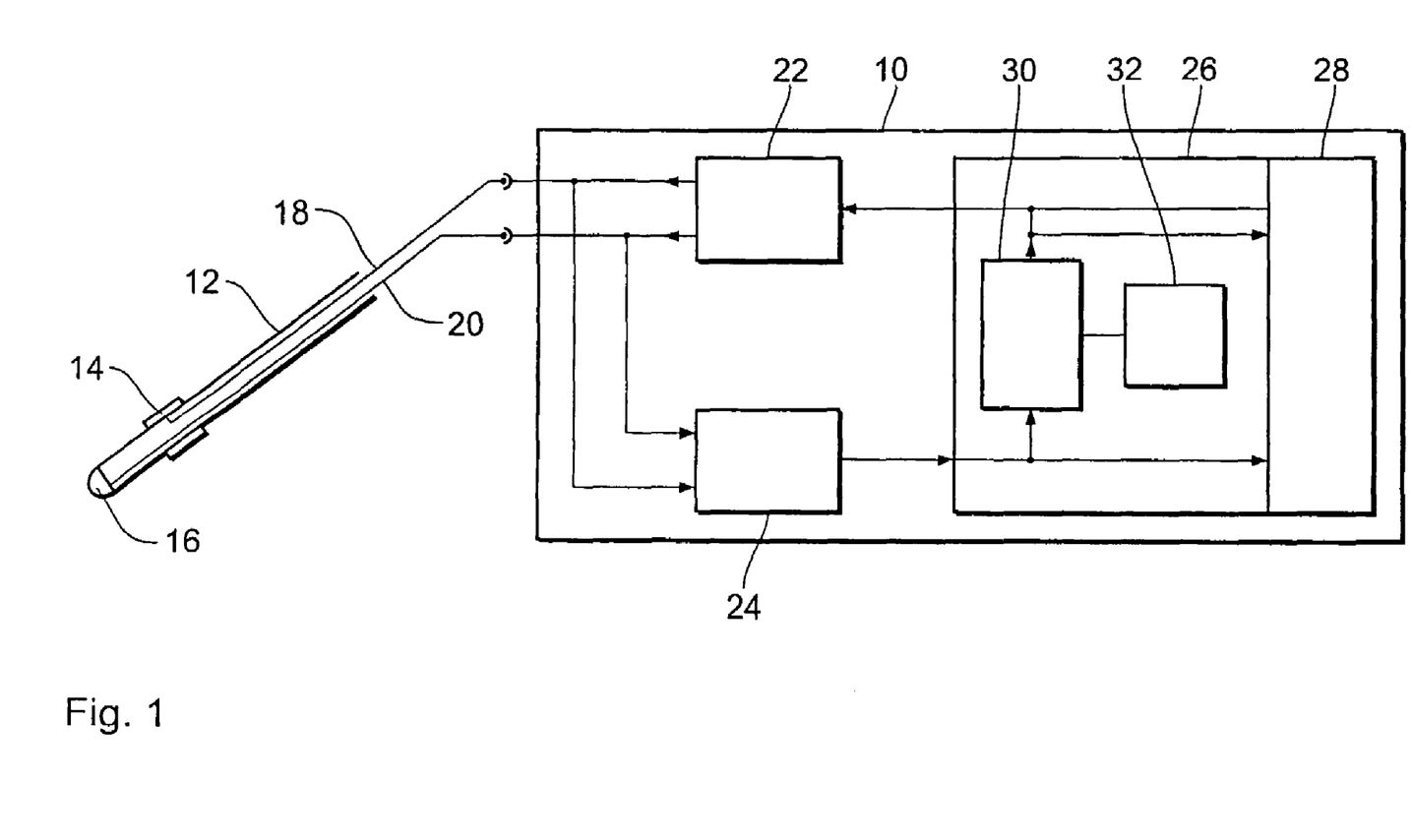
FIG. 1 is a schematic block circuit diagram showing a cardiac pacemaker according to the invention.

FIG. 1 shows a cardiac pacemaker 10 with an electrode line 12 connected thereto. The electrode line 12 is adapted to be introduced for example into a ventricle of a human heart. The electrode line 12 is in the form of a bipolar electrode line and therefore has a ring electrode 14 and a tip electrode 16. The ring electrode 14 and the tip electrode 16 are connected by way of two electric lines 18 and 20 respectively to the pacemaker 10 and in particular a stimulation unit 22 and a detection unit 24 of the pacemaker 10.

The stimulation unit 22 is adapted to deliver bipolar stimulation pulses in the ventricle of a heart by way of the electrodes 14 and 16. Alternatively the stimulation unit 22 may also be connected only by way of one electric line such as the electric line 20 to the tip electrode 16 in order to deliver stimulation pulses in the unipolar mode between a casing of the pacemaker 10 and the tip electrode 16.

The detection unit 24 is connected to the electrodes 14 and 16 to receive electrical signals of the heart. This can also take place as shown in FIG. 1 in the bipolar mode or alternatively in a unipolar mode by way of the tip electrode 16 or the ring electrode 14. The detection unit 24 serves for receiving signals and for adaptation of the measurement signals and possibly impedance conversion. In addition the detection unit 24 controls possible blanking periods or refractory times of the pacemaker 10, in which measured signals are not evaluated or are not even received. The signals are therefore received in time association with stimulation pulses which are possibly delivered by way of the stimulation unit 22. The received signals essentially represent an intracardially produced electrocardiogram which is passed internally of the pacemaker for further evaluation to a control unit 26. The control unit 26 includes a stimulation control unit 28 which serves in per se known manner for actuation of the stimulation unit 22 in dependence on the intracardially obtained signals and possible further signals such as for example physiological control signals for demand-responsive, rate-adaptive stimulation of the heart. The stimulation control unit 28 can also be connected to a sensor in the atrium of a heart in order to implement atrium-synchronous stimulation of the ventricle in known manner. In addition the stimulation control unit 28 affords the per se known function of suppressing the delivery of ventricular stimulation pulses if natural ventricle action is detected within a predetermined time window by way of the detection unit 24. In order to be able to suitably actuate the stimulation unit 22, the stimulation control unit 28 is connected to the stimulation unit 22.

Insofar as the cardiac pacemaker 10 has been described hereinbefore it can be designed in any design configuration known from the state of the art.

An essential feature of the cardiac pacemaker 10 is an evaluation unit 30 to which is fed at the input side thereof an intracardially received signal which for example originates from the detection unit 24. That signal can basically be obtained in any known manner which is suitable for recording ventricular evoked stimulation responses (VER). The evaluation unit 30 is adapted to evaluate the signal at its input from a time after the end of a blanking period which in turn begins with the delivery of a stimulation pulse by the stimulation unit 22. Evaluation of the signal after the expiry of the blanking period is effected with reference to a signal value which obtains during the blanking period. That represents in practice the zero point for further evaluation of the signal. Evaluation of the signal is effected in the manner described in the opening part of this specification, by extraction of the signal features INGR1, INGR2, CNT1, CROSS, MAX_POS and NEG_AMP. In addition the evaluation unit 30 is adapted to execute the algorithm described hereinbefore. For that purpose it is connected to a store or memory 32 for all values to be stored and predetermined, in particular the values w, w1, zn, zp, a1, a2, x and AREA.

The evaluation unit 30 is in particular adapted to compare all sample values NEG_AMP continuously to the limit value zn and, in the event of a positive comparison result, to deliver to the stimulation control unit 28 a capture signal which characterises successful stimulation.

It is essential however that the evaluation unit 30, under the conditions described hereinbefore, also outputs a non-capture signal which characterises unsuccessful stimulation. FIG. 1 illustrates a variant in which that non-capture signal is passed directly to a control line leading to the stimulation unit 22 in order directly to output a backup stimulation pulse if the evaluation unit 30 has detected stimulation failure. That non-capture signal is delivered at the same time to the stimulation control unit 28. It is possible to envisage alternative design configurations in which the evaluation unit 30 delivers a non-capture signal directly to the stimulation unit 22 only in the case of stimulation failure. Another alternative configuration can provide for delivery both of the capture signal and also the non-capture signal or only one of the two signals exclusively directly to the stimulation control unit 28.

Figure 2:
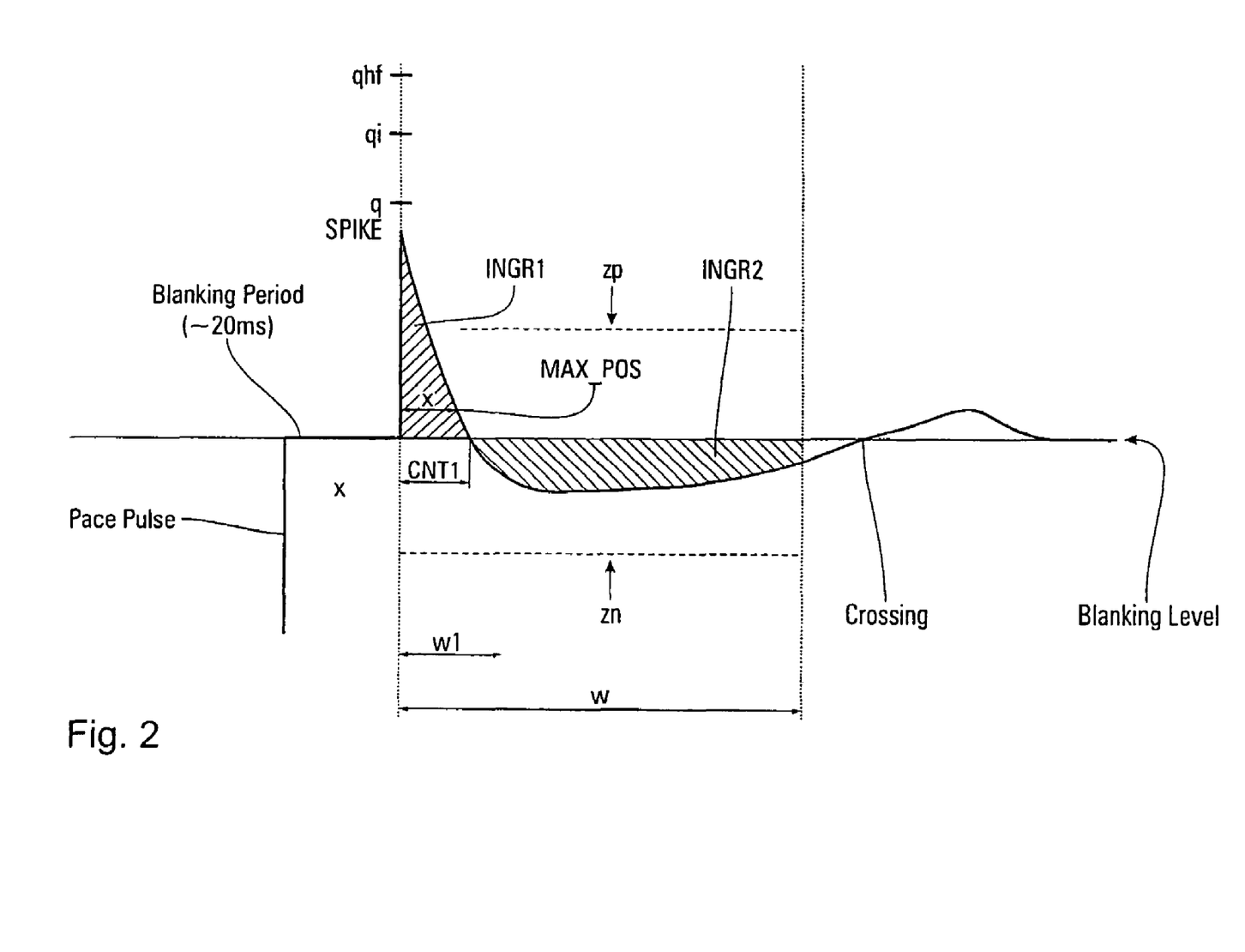
FIG. 2 is a representation of a signal which is typically received after the delivery of a stimulation pulse over time with the typical signal features for a polarisation artefact together with a representation of the preferably received and predetermined signal features and threshold values.

FIG. 2 shows a typical signal shape which goes back to the described polarisation effect, that is to say a polarisation artefact. FIG. 2 plots all the above-mentioned signal features which the evaluation unit 30 is adapted to extract, and all predetermined limit and other values which are stored in the memory 32. In addition the signal amplitude which obtains during the blanking period is plotted as the zero line, as the 'blanking level'. In the illustrated case the blanking period lasts 20 milliseconds after the delivery of a stimulation pulse. The moment in time of delivery of the stimulation pulse is also shown. As can be seen from FIG. 2, the signal received after the end of the blanking period begins with a positive signal peak value and then falls away in order to fall below the signal which obtains during the blanking period, after a given number of sample values (CNT1). The signal which is then negative rises again after some time and crosses the signal level which obtains during the blanking period. If that crossing point is within the time window predetermined by w, the indicator flag is set to 1. If the crossing point is outside the time window predetermined by w—as in the case shown in FIG. 2—the indicator flag CROSS remains zero. Also shown is the positive first integral INGR1 which is the integral of the measurement signal, over time, beginning with the end of the blanking period, to the first negative zero-passage of the signal, and the second integral INGR2 which represents the remaining area integral of the measurement signal in the time window predetermined by w, in relation to the signal amplitude which obtains during the blanking period.

Figure 3:
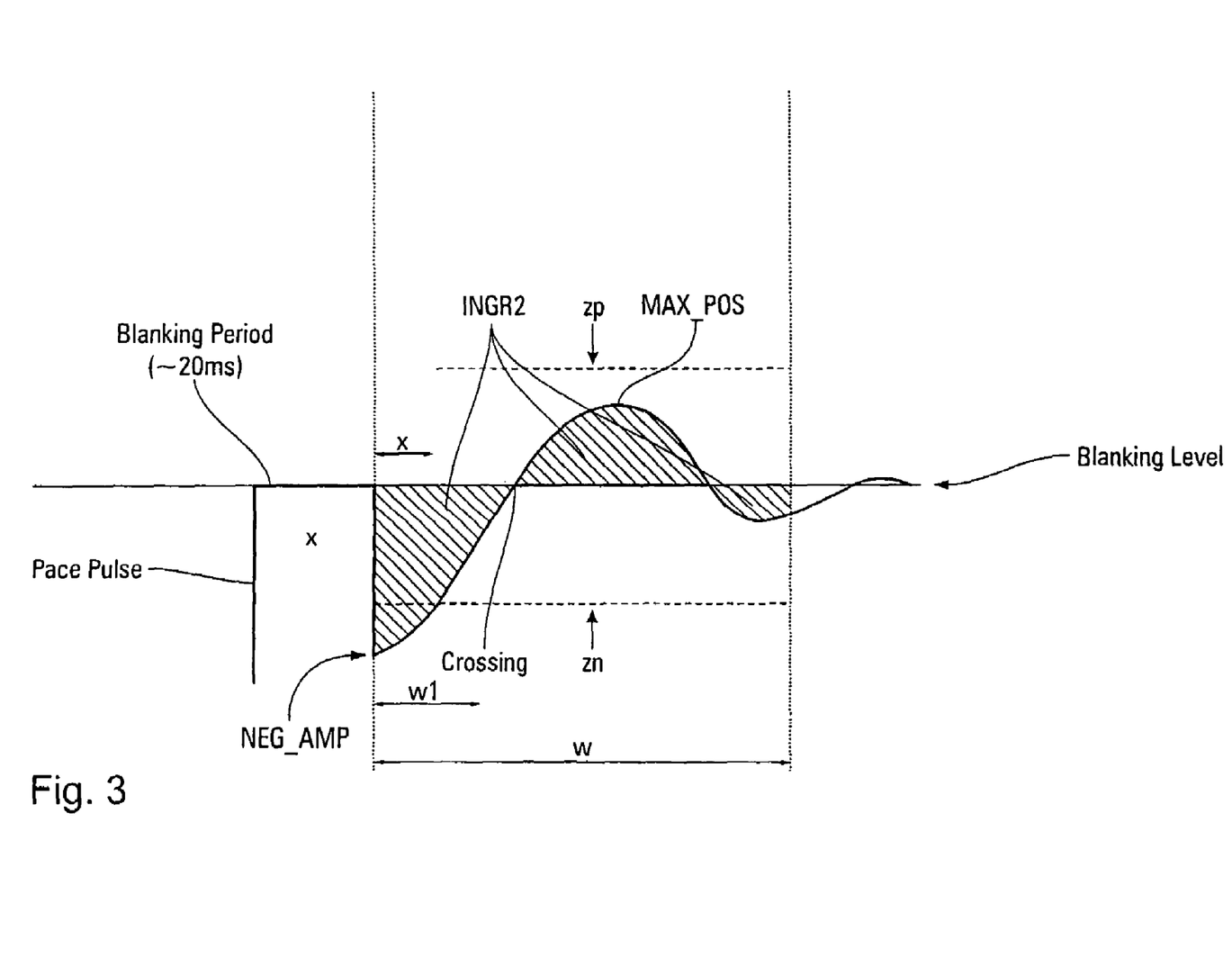
FIG. 3 is a diagrammatic representation of a typical signal shape of a signal received after a stimulation pulse in the case of a successful stimulation with the associated received signal features and threshold values.

FIG. 3 shows the typical configuration of an evoked stimulation response and all parameters described hereinbefore. The extracted signal features are shown as before in capital letters while the limit values and other parameters which are to be predetermined are identified by lower-case letters. The signal which is shown in FIG. 3 and which characterises a positive stimulation success begins with a negative amplitude whose negative amount is greater than the limit value zn. It is therefore already established with the first sample value that the signal is to be attributed to a positive stimulation success so that the evaluation unit 30 can already break off the above-described algorithm, with the first sample value, and output a capture signal.

Figure 4:
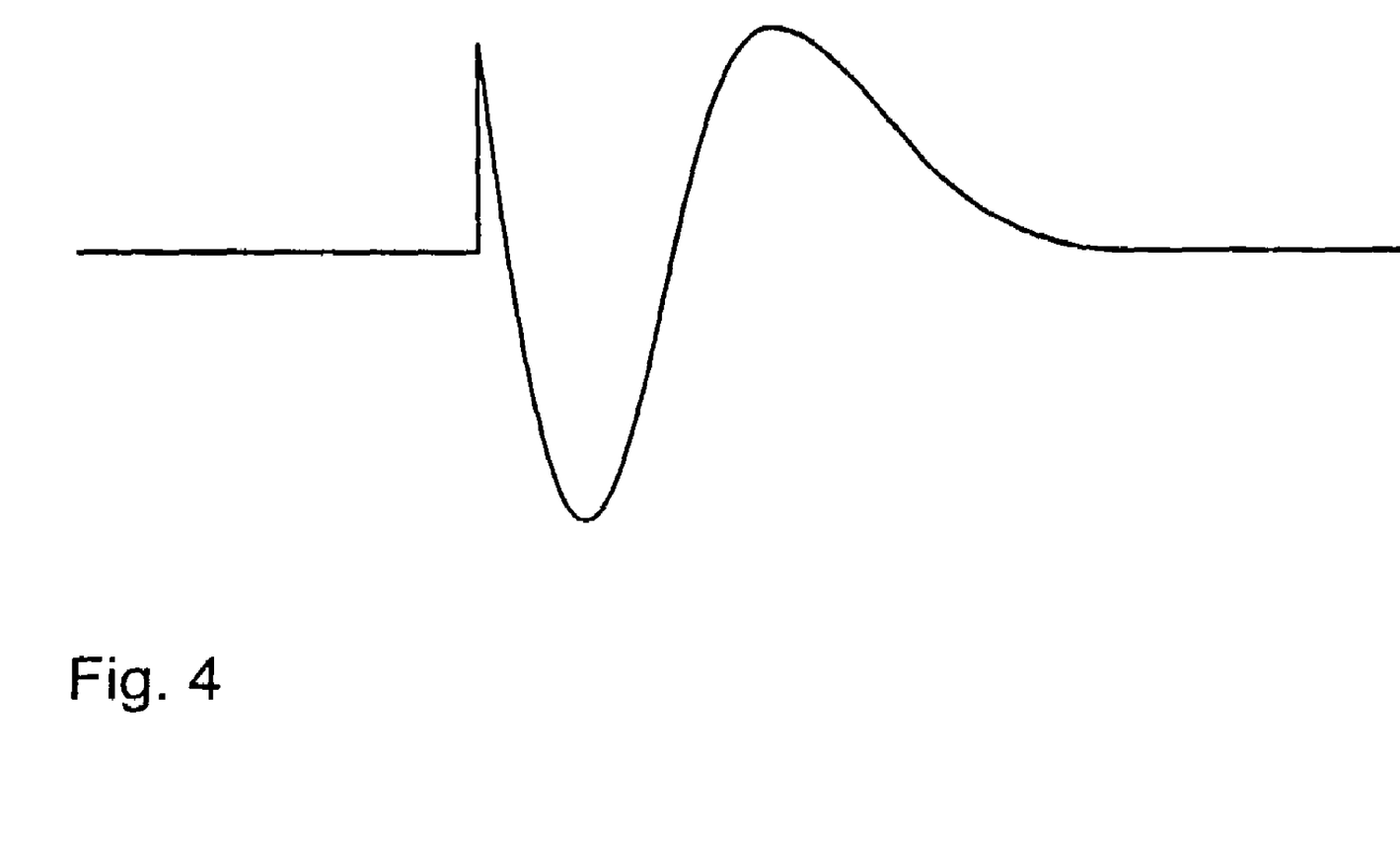
FIG. 4 shows a signal shape of the received signal after successful stimulation with initial positive amplitude.

As shown in FIG. 4 the signal obtained in the case of stimulation success can also begin with a positive signal peak value. In this case also the evaluation unit 30 permits reliable recognition of a stimulation failure and in the case of the signal shape shown in FIG. 4 outputs not a non-capture but a capture signal.

The invention also goes beyond the variant illustrated in the specific embodiment to all other variants which are obvious to the man skilled in the art, such as for example the variant already indicated hereinbefore, in which the evaluation unit 30 directly actuates the stimulation unit 22 in the non-capture situation in order to trigger a backup stimulation pulse with a higher energy level than the preceding stimulation pulse.

The invention claimed is:

1. A stimulation arrangement, comprising:
   a stimulation unit to deliver electrical stimulation pulses for stimulating body tissue; and
   an evaluation unit to receive at least one electrical signal in conjunction with the delivery of a stimulation pulse and to evaluate said received electrical signal for checking both stimulation success and lack of stimulation success, and wherein the evaluation unit is capable of detecting first signal features in the received electrical signal that characterize a case of lack of stimulation success, and delivering a corresponding first output signal, and wherein the evaluation unit is capable of detecting second signal features in the received electrical signal that characterize a case of stimulation success, and delivering a corresponding second output signal; and wherein the evaluation unit associates the received signal with a stimulation pulse in respect of time and detects a feature of a polarization artifact as a signal feature in the received electrical signal.

2. The stimulation arrangement of claim 1, wherein the evaluation unit evaluates the received electrical signal measured after the expiry of a blanking period after the delivery of a stimulation pulse to determine a first integral (INGR1) of the measured signal over a first time interval in which the measured signal extends above a blanking level measured during the blanking period.

3. The stimulation arrangement of claim 2, wherein the evaluation unit continuously compares sample values of said received electrical signal to a limit value (zn) for negative signal amplitude and delivers a signal which characterizes a stimulation success in the case of the limit value (zn) being negatively exceeded by at least one of said sample values.

4. The stimulation arrangement of claim 2, wherein the evaluation unit determines a second integral (INGR2) of the measured signal over a second time interval beginning with an end of said first time interval and extending to an end of a predetermined time window whose beginning is an end of the blanking period.

5. The stimulation arrangement of claim 4, wherein the evaluation unit continuously compares sample values of said received electrical signal to a limit value (zn) for negative signal amplitude and delivers a signal which characterizes a stimulation success in the case of the limit value (zn) being negatively exceeded by at least one of said sample values.

6. The stimulation arrangement of claim 4, wherein the evaluation unit forms an indicator flag (CROSS) having a binary value that depends on whether the measured signal during the second time interval crosses the measured blanking level.

7. The stimulation arrangement of claim 6, wherein the evaluation unit continuously compares said sample values of said received electrical signal to a limit value (zn) for negative signal amplitude and delivers a signal that characterizes a stimulation success in the case of the limit value (zn) being negatively exceeded by at least one of said sample values.

8. The stimulation arrangement of claim 6 wherein an area value (AREA) is calculated as a sum of said INGR1 and said INGR2 if said CNT1 is greater than a predetermined sample number limit value (w1), and wherein said area value (AREA) is calculated as said INGR2 if said CNT1 is less than or equal to said w1.

9. The stimulation arrangement of claim 8 wherein said evaluation unit delivers a signal that characterizes a lack of stimulation success if said AREA is determined to be less than a first predetermined area limit value (a1).

10. The stimulation arrangement of claim 9 wherein said evaluation unit delivers a signal that characterizes a lack of stimulation success if said CNT1 is greater than said w1 and if a maximum positive sample value (MAX_POS) of said measured signal, measured at least x samples after said blanking period, is less than a predetermined amplitude limit value (zp), and where x is a predetermined number of samples.

11. The stimulation arrangement of claim 10 wherein said evaluation unit delivers a signal that characterizes a stimulation success if said CNT1 is greater than said w1 and if said maximum positive sample value (MAX_POS) of said measured signal, measured at least x samples after said blanking period, is greater than or equal to said predetermined amplitude limit value (zp).

12. The stimulation arrangement of claim 11 wherein said evaluation unit delivers a signal that characterizes a stimulation success if said AREA is greater than a second predetermined area limit value (a2).

13. The stimulation arrangement of claim 12 wherein said evaluation unit delivers a signal that characterizes a stimulation success if said CROSS is equal to a binary value indicating that said measured signal has crossed said measured blanking level during said second time interval.

14. The stimulation arrangement of claim 13 wherein said evaluation unit delivers a signal that characterizes a lack of stimulation success.

15. The stimulation arrangement of claim 2, wherein the received electrical signal received after the delivery of said stimulation pulse is received in a form of time-discrete sample values, and wherein the evaluation unit further comprises a counter that determines a number (CNT1) of said sample values of the received electrical signal, which fall into the first time interval over which the first integral is formed.

16. The stimulation arrangement of claim 15, wherein the evaluation unit continuously compares said sample values of said received electrical signal to a limit value (zn) for negative signal amplitude and delivers a signal which characterizes a stimulation success in the case of the limit value (zn) being negatively exceeded by at least one of said sample values.

17. The stimulation arrangement of claim 1, wherein the evaluation unit continuously compares sample values of said received electrical signal to a limit value (zn) for negative signal amplitude and delivers a signal which characterizes a stimulation success in the case of the limit value (zn) being negatively exceeded by at least one of said sample values.

18. The stimulation arrangement of claim 1, wherein the evaluation unit continuously compares sample values of said received electrical signal to a limit value (zn) for negative signal amplitude and delivers a signal which characterizes a stimulation success in the case of the limit value (zn) being negatively exceeded by at least one of said sample values.

19. A stimulation arrangement, comprising:

a stimulation unit to deliver electrical stimulation pulses for stimulating body tissue; and an evaluation unit to receive at least one electrical signal in conjunction with the delivery of a stimulation pulse and to evaluate said received electrical signal for checking both stimulation success and lack of stimulation success, and wherein the evaluation unit is capable of detecting first signal features in the received electrical signal that characterize a case of lack of stimulation success, and delivering a corresponding first output signal, and wherein the evaluation unit is capable of detecting second signal features in the received electrical signal that characterize a case of stimulation success, and delivering a corresponding second output signal, wherein the evaluation unit continuously compares sample values of said received electrical signal to a limit value (zn) for negative signal amplitude and delivers a signal which characterizes a stimulation success in the case of the limit value (zn) being negatively exceeded by at least one of said sample values.

* * * * *